United States Patent [19]
Morton et al.

[11] Patent Number: 5,376,688
[45] Date of Patent: Dec. 27, 1994

[54] ENHANCED SOLUBILITY PHARMACEUTICAL SOLUTIONS

[75] Inventors: Frank S. S. Morton, Seminole; Rickey S. Shelley, Largo, both of Fla.; Mahendra S. Patel, Zaventem, Belgium

[73] Assignee: R. P. Scherer Corporation, Troy, Mich.

[21] Appl. No.: 993,305

[22] Filed: Dec. 18, 1992

[51] Int. Cl.$^5$ .................. A61K 47/00; A61K 47/32; A61K 9/48
[52] U.S. Cl. .................. 514/786; 514/769; 514/772; 514/772.4; 514/772.5; 424/452
[58] Field of Search .............. 514/772, 772.1, 786, 514/769, 772.4, 772.5; 424/455, 456, 452, 722

[56] References Cited

U.S. PATENT DOCUMENTS

| | | | |
|---|---|---|---|
| 4,188,373 | 2/1980 | Krezanoski | 424/78 |
| 4,744,988 | 5/1988 | Brox | 424/456 |
| 4,780,316 | 10/1988 | Brox | 424/456 |
| 4,888,239 | 12/1989 | Brox | 428/402.2 |
| 5,071,643 | 12/1991 | Yu et al. | 424/455 |
| 5,141,961 | 8/1992 | Coapman | 514/629 |
| 5,200,191 | 4/1993 | Steele et al. | 424/453 |

FOREIGN PATENT DOCUMENTS

WO8802625 4/1988 WIPO.
WO9300891 1/1993 WIPO.

OTHER PUBLICATIONS

Patel et al., "Factors Affecting The Chemical Stability Of Carboxylic Acid Drugs In Enhanced Solubility System (ESS) Softgel Formulations Based On Polyethylene Glycol (PEG)," Drug Development and Industrial Pharmacy, 18(1), 1–19 (Jan., 1992).

Primary Examiner—Raymond J. Henley
Attorney, Agent, or Firm—Allegretti & Witcoff, Ltd.

[57] ABSTRACT

Pharmaceutically acceptable solutions of acidic, basic or amphoteric pharmaceutical agents are disclosed. These solutions are suitable for encapsulation in gelatin capsules for subsequent oral administration and include the pharmaceutical agent, an ion species and a solvent system.

18 Claims, No Drawings

ENHANCED SOLUBILITY PHARMACEUTICAL SOLUTIONS

BACKGROUND OF THE INVENTION

1. Field of the Invention

The present invention relates to solutions containing acidic, basic and/or amphoteric pharmaceutical agents for encapsulation in gelatin capsules.

2. Description of the Art

Soft gelatin capsules and hard shell gelatin capsules are well known for the oral administration of pharmaceutical agents. For pharmaceutical agents of relatively low solubility and/or relatively high dosage amount, gelatin capsules can pose problems for the pharmaceutical formulator. For example, if a given pharmaceutical agent has a relatively low solubility, it may need a relatively large volume of solution in order to deliver a unit dose. While it is may be possible to encapsulate such a large volume of solution in a soft gelatin capsule, for example, the resulting capsule may be too large for conventional oral administration to human patients.

In similar fashion, if a pharmaceutical agent requires a relatively high dose, a large volume of solution may be necessary in order to deliver this dose. Encapsulation of this large volume may result in a capsule that is too large for convenient oral administration to human patients.

As one approach to solving this problem in the capsule formulation art, U.S. Pat. No. 5,071,643 (Yu, et al.) discloses the use of polyethylene glycol based solutions for acidic, basic and amphoteric pharmaceutical agents. These polyethylene glycol based solutions contain either an hydroxide species or a hydrogen ion species that causes the appropriate pharmaceutical agent to partially ionize, i.e., the pharmaceutical agent is present in both the free form and the salt form. The partial ionization described in Yu, et al. results in enhanced solubility for the acidic, basic or amphoteric pharmaceutical agent. This enhanced solubility, in turn, may permit the preparation of a solution of pharmaceutical agent that is highly concentrated enough to be encapsulated in a conveniently sized gelatin capsule for oral administration. The Yu, et al. patent discloses that enhanced solubility solutions can be prepared using polyethylene glycol and contemplated equivalents of polyethylene glycol, such as polyethylene glycol ethers of various alcohols and copolymers of polyethylene glycol.

The present inventors have discovered that other solvents may be used to form pharmaceutically acceptable solutions that exhibit enhanced solubility characteristics. These enhanced solubility pharmaceutical solutions have the advantages contemplated by Yu, et al., i.e., encapsulation of dosages in small capsules.

SUMMARY OF THE INVENTION

It is an object of the present invention to form enhanced solubility pharmaceutically acceptable solutions of acidic, basic and amphoteric pharmaceutical agents suitable for encapsulation in gelatin capsules for subsequent oral administration.

It is a specific object of the present invention to provide pharmaceutically acceptable solutions containing an acidic pharmaceutical agent, a hydroxide species and a solvent system. The hydroxide species is capable of dissociating into pharmaceutically acceptable cations and hydroxide ions. The hydroxide species is present in the solution such that between about 0.05 and less than about 1.5 moles of hydroxide ions per mole of acidic groups in the acidic pharmaceutical agent are present in the solution. The hydroxide species partially ionizes the acidic pharmaceutical agent so that the acidic drug is present in a dissolved state in the solution as both a free acid and as a cationic salt. Furthermore, the acidic drug is present in a solubility enhanced amount, i.e., a concentration greater than the maximum solubility of the acidic pharmaceutical agent in the solution in the absence of the hydroxide species.

For use with basic pharmaceutical agents, a hydrogen ion species is substituted for the hydroxide species used with the acidic pharmaceutical agent. The hydrogen ion species is capable of dissociating into pharmaceutically acceptable anions and hydrogen ions. The hydrogen ion species is present in an amount so that between about 0.05 and less than about 1.5 moles of hydrogen ions per mole of basic groups in the basic pharmaceutical agent are present in the solution. As with the embodiment of the present invention concerning acidic pharmaceutical agents, the hydrogen ion species partially ionizes the basic pharmaceutical agent so that the basic pharmaceutical agent is present in a dissolved state in the solution as both a free base and an anionic salt. The basic pharmaceutical agent is present in a solubility enhanced amount that is greater than the maximum solubility of the basic pharmaceutical agent in the solution in the absence of the hydrogen ion species.

In connection with amphoteric pharmaceutical agents, either a hydrogen ion species or a hydroxide species may be used. The selected ion species is present in an amount so that between about 0.05 and less than about 1.5 moles of ions per mole of ionizable groups in the amphoteric pharmaceutical agent are present in the solution. The ion species then partially ionizes the pharmaceutical agent such that the amphoteric pharmaceutical agent is present in a dissolved state in the solution in both a free form and as a salt. The solubility of the amphoteric pharmaceutical agent is enhanced to an amount greater than the maximum solubility of the amphoteric pharmaceutical agent in the solution in the absence of the ion species.

The solvent system contemplated in the present invention consists primarily of or essentially of a solvent selected from the group consisting of diethylene glycol monoethyl ether, glycerol caprylate/caprate, polyglycerol oleate, alpha-hydro-w-hydroxypoly(oxyethylene)-poly(oxypropylene)-poly(oxyethylene) block copolymers and mixtures thereof.

The inventive solutions may contain optional, additional ingredients, such as water, glycerin, propylene glycol, alcohols and/or polyvinylpyrrolidone. The present invention also contemplates the use of solvent systems including polyethylene glycol as an additional cosolvent, as well as solvent systems comprising a blend of polyethylene glycol and polyoxyethylene sorbitan esters, such as polyoxyethylene sorbitan mono-oleate and/or polyoxyethylene sorbitan monolaurate, as well as other equivalent solvent systems.

Further objects and embodiments of the present invention will be described in the following description of the preferred embodiments.

DESCRIPTION OF THE PREFERRED EMBODIMENTS

The disclosure of U.S. Pat. No. 5,071,643 (Yu, et al.) is incorporated herein in its entirety. The disclosure in the Yu, et al. patent is relevant to the present invention in that the Yu, et al. formulations involve partial ionization of acidic, basic and amphoteric drugs. Of course, the teachings of Yu, et al. cannot be directly applied in all particulars, since the solvent system in the present invention differs from that in Yu, et al. Specifically, Yu, et al. uses polyethylene glycol and contemplated equivalents of polyethylene glycol. By contrast, the present invention is directed to the use of alternative solvent systems. With this caveat, the disclosure contained in Yu, et al. and incorporated herein by reference is generally applicable to the present invention with the substitution of the inventive solvents for polyethylene glycol.

A wide variety of acidic, basic and amphoteric pharmaceutical agents may be used in connection with the present invention. Exemplary of the acidic pharmaceutical agents that are useful are ibuprofen, naproxen, ketoprofen, indomethacin, and acetaminophen. Exemplary of the basic pharmaceutical agents are pseudoephedrinc, ranitidine, thioridazine and cimetidine. Exemplary of the amphoteric pharmaceutical agents are methyldopa and enalapril.

In the present inventive solutions, the acidic, basic or amphoteric pharmaceutical agent is present in a partially ionized form. In other words, the pharmaceutical agent is present in both the free form and the salt form. The additive nature of the concentration gradients of these two forms results in enhanced solubility of the pharmaceutical agent in the solution. This enhanced solubility is demonstrated by solubilities that exceed the maximum solubility of the pharmaceutical agent in the solution in the absence of the specified ion species.

An important aspect of the present invention is that the ion species is appropriately matched to the pharmaceutical agent. More specifically, acidic pharmaceutical agents must be partially ionized with hydroxide species. Basic pharmaceutical agents must be solubilized with hydrogen ion species. Amphoteric pharmaceutical agents, on the other hand, can be partially ionized with either a hydroxide species or a hydrogen ion species.

In order to achieve partial ionization, an appropriate balance should be struck between the moles of ionizable groups in the particular pharmaceutical agent and the moles of specified ion species. In acidic pharmaceutical agents, the hydroxide species should desirably be present in amounts such that between about 0.05 and less than about 1.5 (more preferably between about 0.3 and about 1.2) moles of hydroxide ions per mole of acidic groups in the acidic pharmaceutical agent are present in the solution. Similarly, for basic pharmaceutical agents, the hydrogen ion species should desirably be present in an amount such that between about 0.05 and less than about 1.5 (more preferably between about 0.3 and about 1.2) moles of hydrogen ions per mole of basic groups in the basic pharmaceutical agent are present in the solution. Finally, in the case of amphoteric pharmaceutical agents, the ion species selected should desirably be present in an amount such that between about 0.05 and less than about 1.5 (more preferably between about 0.3 and about 1.2) moles of ions selected from the group consisting of hydrogen ions and hydroxide ions per mole of ionizable groups in the amphoteric pharmaceutical agent are present in the solution.

In general, any pharmaceutically acceptable source of hydroxide ions may be used with acidic and amphoteric pharmaceutical agents. The source of hydroxide ions should desirably not interact with the selected pharmaceutical agent except to the extent of causing partial ionization. Preferred sources of hydroxide ions are alkali hydroxides such as sodium hydroxide and potassium hydroxide.

In similar fashion, any pharmaceutically acceptable source of hydrogen ions may be used as the hydrogen ion species in connection with basic and amphoteric pharmaceutical agents. The selected hydrogen ion species should desirably not interact with the selected pharmaceutical agent except to the extent of causing partial ionization. Preferred sources of hydrogen ions include mineral acids such as hydrochloric acid and organic acids such as citric acid.

The solvent systems useful in the present invention consist primarily of or consist essentially of one of the following solvents or mixtures thereof: diethylene glycol monoethyl ether, glycerol caprylate/caprate, polyglycerol oleate and alpha-hydro-w-hydroxypoly(oxyethylene)-poly(oxypropylene)-poly(oxyethylene) block copolymers. Polyglycerol oleate is available under the trade name Plurol Oleique from Gattefosse Establishment, France. Glycerol caprylate/caprate is available under the trade name Labrasol from Gattefosse Establishment, France. Diethylene glycol monoethyl ether is available under the trade name Transcutol from Gattefosse Establishment, France. Finally, alpha-hydro-w-hydroxypoly(oxyethylene)-poly(oxypropylene)-poly(oxyethylene) block polymers are available from BASF, Parsippany, N.J. under the Pluronics trade name. A preferred Pluronic is Pluronic L62 in which $a=7$, $b=30$ and $c=7$ in the following formula: $HO(CH_2CH_2O)_a(CH(CH_3)CH_2OH)_b(CH_2CH_2O)_cH$.
Another preferred Pluronic type material is Synperonic L64 in which $a=20$, $b=23$ and $c=20$.

Polyethylene glycol can be present in admixture with one or more of the above identified solvents to form the solvent system of the present invention. In addition, polyoxyethylene sorbitan esters in combination with polyethylene glycol may be used as the solvent system for the present invention. These sorbitan esters are sold under the trade name Tween. Particularly useful Tweens are polyoxyethylene (20) sorbitan mono-oleate (Tween 80) and polyoxyethylene (20) sorbitan mono-laurate (Tween 20).

The pharmaceutical agent will typically be present in the solution in amounts from about 10% up to about 80% by weight of the solution. However, less concentrated pharmaceutical solutions also fall within the scope of the invention as long as they demonstrate enhanced solubility.

The solvent system will typically be present in amounts ranging from about 10% to about 80% by weight of the solution. In the case of solvent systems including mixtures of different individual solvents, the different solvents can be present in any ratio with respect to each other.

In addition to the pharmaceutical agent, the ion species and the solvent system, other adjuncts may be present. Water may be included in the solution up to about 20% by weight of the solution. More preferred amounts of water range between about 1% up to about 10% by weight of the solution.

Other adjuncts that may enhance the solubility of the particular pharmaceutical agents in the solvent system are glycerin, propylene glycol and polyvinylpyrrolidone. Glycerin or propylene glycol are desirably present in amounts from about 4% up to about 12% by weight of the solution. Polyvinylpyrrolidone is desirably present in amounts from about 1% up to about 20% by weight of the solution. The polyvinylpyrrolidones that are most advantageous have average molecular rates between about 10,000 and about 100,000. When used, polyethylene glycol desirably has average molecular weights of between about 200 and 100,000.

Once the appropriate pharmaceutically acceptable solution is formulated, it can be encapsulated into conventional soft gelatin capsules in accordance with the rotary die process. Alternatively, semi-solid or solid solutions can be appropriately encapsulated in hard shell gelatin capsules as well as soft gelatin capsules.

EXAMPLE 1

The following saturated ibuprofen solutions were prepared containing the indicated weight percent of ibuprofen, the indicated solvent system and the indicated amount of potassium hydroxide. In each case, enhanced solubility is shown at all concentrations of the hydroxide species. The solutions are all suitable for filling into soft gelatin capsules.

| SOLVENT SYSTEM | IBUPROFEN SOLUBILITY (%) MOLE EQUIVALENT HYDROXIDE | | | | |
|---|---|---|---|---|---|
| | 0 | 0.25 | 0.5 | 0.75 | 1.0 |
| TRANSCUTOL | 42.5 | 55.0 | 60.0 | 52.5 | 52.5 |
| LABRASOL | 25.0 | 40.0 | 45.0 | 42.5 | 40.0 |
| PLURONIC L62 | 10.0 | 15.0 | 20.0 | 27.5 | 30.0 |
| PLUROL OLEIQUE | 15.0 | — | 30.0 | — | — |

EXAMPLE 2

The following saturated pseudoephedrine solutions were prepared with the indicated of pseudoephedrine in solution, the indicated solvent and the indicated amount of hydrochloric acid. With the exception of the Transcutol formulations containing higher amounts of hydrochloric acid, enhanced solubility was demonstrated for all formulations. These formulations are suitable for filling into soft gelatin capsules.

| SOLVENT SYSTEM | PSEUDOEPHEDRINE SOLUBILITY (%) MOLE EQUIVALENT ACID | | | | |
|---|---|---|---|---|---|
| | 0 | 0.25 | .5 | 0.75 | 1.0 |
| TRANSCUTOL | 13.0 | 16.3 | 12.8 | 12.3 | 12.1 |
| LABRASOL | 4.0 | 9.0 | 4.7 | — | — |
| PLUROL OLEIQUE | 8.0 | — | 9.7 | — | — |

EXAMPLE 3

The following saturated aspartame solutions were prepared, using aspartame as a model of an amphoteric pharmaceutical agent. These solutions contain the indicated amount of aspartame, the indicated solvent and the indicated amount of potassium hydroxide. Except for Pluronic L62, the aspartame showed enhanced solubility in the presence of the hydroxide species. The solutions were suitable for filling into soft gelatin capsules.

| SOLVENT SYSTEM | ASPARTAME SOLUBILITY (%) MOLE EQUIVALENT HYDROXIDE | |
|---|---|---|
| | 0 | 0.50 |
| TRANSCUTOL | 0.43 | 0.68 |
| LABRASOL | 0.30 | 0.60 |
| PLURONIC L62 | 0.045 | 0.045 |

EXAMPLE 4

The following saturated aspartame solutions were made using aspartame for a model for an amphoteric pharmaceutical agent. The solutions contain the indicated amount of aspartame, the indicated solvent and the indicated amount of hydrochloric acid. In each instance, enhanced solubility was noted. These solutions are suitable for filling into soft gelatin capsules.

| SOLVENT SYSTEM | ASPARTAME SOLUBILITY (%) MOLE EQUIVALENT ACID | |
|---|---|---|
| | 0 | 50 |
| TRANSCUTOL | 0.43 | 0.91 |
| LABRASOL | 0.30 | 0.50 |
| PLURONIC L62 | 0.045 | 0.095 |

EXAMPLE 5

The following naproxen solutions were prepared containing the indicated ingredients in mg.

| | A | B | C |
|---|---|---|---|
| Naproxen | 250.0 | 250.0 | 250.0 |
| 50% KOH Solution | 57.3 | 57.3 | 57.3 |
| Water | 13.4 | 13.4 | 13.4 |
| Glycerin | 54.2 | 54.2 | 54.2 |
| PEG 600 | 355.0 | 355.0 | 328.0 |
| Tween 80 | 355.0 | — | — |
| Tween 20 | — | 355.0 | 54.2 |
| Synperonic L64 | — | — | 328.0 |

EXAMPLE 6

The following ketoprofen formulation was prepared with the following composition in mg:

| Ketoprofen | 50.0 |
|---|---|
| 50% KOH Solution | 10.4 |
| Glycerin | 10.0 |
| Water | 3.1 |
| PEG 600 | 68.0 |
| Synperonic L64 | 68.0 |

Certain specific embodiments of the present invention have been discussed and disclosed in detail. Many other embodiments that have not been disclosed or described are nevertheless the equivalent of and fall within the scope of the present invention and/or the following claims.

We claim:

1. A pharmaceutically acceptable solution of an acidic pharmaceutical agent suitable for encapsulation in gelatin capsules for subsequent oral administration comprising, the acidic pharmaceutical agent, a hydroxide species and a solvent system, the solvent system consisting essentially of a solvent selected from the group consisting of diethylene glycol monoethyl ether, polyglycerol oleate, and mixtures thereof, the hydroxide species being capable of dissociating into pharmaceutically acceptable cations and hydroxide ions, the hydroxide species being present in an amount such that between about 0.05 and less than about 1.5 moles of hydroxide ions per mole of acidic groups in the acidic pharmaceutical agent are present in the solution, the hydroxide species partially ionizing the acidic pharmaceutical agent such that the acidic pharmaceutical agent is present in a dissolved state in the solution as both a free acid and a cationic salt in a solubility enhanced amount greater than the maximum solubility of the acidic pharmaceutical agent in the solution in the absence of the hydroxide species.

2. The solution of claim 1 wherein the hydroxide species is potassium hydroxide.

3. The solution of claim 1 wherein the solvent system additionally includes polyethylene glycol.

4. The solution of claim 1 additionally comprising from about 1% to about 20% water by weight of the solution.

5. The solution of claim 1 additionally comprising glycerin, propylene glycol or polyvinylpyrrolidone.

6. A pharmaceutically acceptable solution of a basic pharmaceutical agent suitable for encapsulation in gelatin capsules for subsequent oral administration comprising, the basic pharmaceutical agent, a hydrogen ion species and a solvent system, the solvent system consisting essentially of a solvent selected from the group consisting of diethylene glycol monoethyl ether, polyglycerol oleate, and mixtures thereof, the hydrogen ion species being capable of dissociating into pharmaceutically acceptable anions and hydrogen ions, the hydrogen ion species being present in an amount such that between about 0.05 and less than about 1.5 moles of hydrogen ions per mole of basic groups in the basic pharmaceutical agent are present in the solution, the hydrogen ion species partially ionizing the basic pharmaceutical agent such that the basic pharmaceutical agent is present in a dissolved state in the solution as both a free base and an anionic salt in a solubility enhanced amount greater than the maximum solubility of the basic pharmaceutical agent in the solution in the absence of the hydrogen ion species.

7. The solution of claim 6 wherein the hydrogen ion species is hydrochloric acid.

8. The solution of claim 6 wherein the solvent system additionally includes polyethylene glycol.

9. The solution of claim 6 additionally comprising from about 1% to about 20% water by weight of the solution.

10. The solution of claim 6 additionally comprising glycerin, propylene glycol or polyvinylpyrrolidone.

11. A pharmaceutically acceptable solution of an amphoteric pharmaceutical agent suitable for encapsulation in gelatin capsules for subsequent oral administration comprising, the amphoteric pharmaceutical agent, an ion species selected from the group consisting of cationic hydroxide species and anionic hydrogen ion species, and a solvent system, the solvent system consisting essentially of a solvent selected from the group consisting of diethylene glycol monoethyl ether, polyglycerol oleate, and mixtures thereof, the ion species being capable of dissociating in the solution into pharmaceutically acceptable ions, the ion species being present in an amount such that between about 0.05 and less than about 1.5 moles of ions selected from the group consisting of hydrogen ions and hydroxide ions per mole of ionizable groups in the amphoteric pharmaceutical agent are present in the solution, the ion species partially ionizing the amphoteric pharmaceutical agent such that the amphoteric pharmaceutical agent is present in a dissolved state in the solution in both free form and as a salt in a solubility enhanced amount greater than the maximum solubility of the amphoteric pharmaceutical agent in the solution in the absence of the ion species.

12. The solution of claim 11 wherein the ion species is potassium hydroxide or hydrochloric acid.

13. The solution of claim 11 wherein the solvent system additionally includes polyethylene glycol.

14. The solution of claim 11 additionally comprising from about 1% to about 20% water by weight of the solution.

15. The solution of claim 11 additionally comprising glycerin, propylene glycol or polyvinylpyrrolidone.

16. A gelatin capsule comprising a gelatin shell and a fill material disposed within the shell, the fill material comprising (a) from about 0–20% water; and (b) a solution of an acidic pharmaceutical agent comprising the acidic pharmaceutical agent, a hydroxide species and a solvent system, the solvent system consisting essentially of a solvent selected from the group consisting of diethylene glycol monoethyl ether, polyglycerol oleate, alpha-hydro-w-hydroxypoly(oxyethylene)-poly(oxypropylene)-poly(oxyethylene) block copolymers, and mixtures thereof, the hydroxide species being capable of dissociating into pharmaceutically acceptable cations and hydroxide ions, the hydroxide species being present in an amount such that between about 0.05 and less than about 1.5 moles of hydroxide ions per mole of acidic groups in the acidic pharmaceutical agent are present in the solution, the hydroxide species partially ionizing the acidic pharmaceutical agent such that the acidic pharmaceutical agent is present in a dissolved state in the solution as both a free acid and a cationic salt in a solubility enhanced amount greater than the maximum solubility of the acidic pharmaceutical agent in the solution in the absence of the hydroxide species.

17. A gelatin capsule comprising a gelatin shell and a fill material disposed within the shell, the fill material comprising:

(a) from about 0–20% of water; and (b) a solution of a basic pharmaceutical agent comprising the basic pharmaceutical agent, a hydrogen ion species and a solvent system, the solvent system consisting essentially of a solvent selected from the group consisting of diethylene glycol monoethyl ether, polyglycerol oleate, alpha-hydro-w-hydroxypoly(oxyethylene)-poly(oxypropylene)-poly(oxyethylene) block copolymers, and mixtures thereof, the hydrogen ion species being capable of dissociating into pharmaceutically acceptable anions and hydrogen ions, the hydrogen ion species being present in an amount such that between about 0.05 and less than about 1.5 moles of hydrogen ions per mole of basic groups in the basic pharmaceutical agent are present in the solution, the hydrogen ion species partially ionizing the basic pharmaceutical agent such that the basic pharmaceutical agent is present in a dissolved state in the solution as both a free base and an anionic salt in a solubility enhanced amount greater than the maximum solubility of the basic pharmaceutical agent in the solution in the absence of the hydrogen ion species.

18. A gelatin capsule comprising a gelatin shell and a fill material disposed within the shell, the fill material comprising:

(a) from about 0–20% of water; and
(b) a solution comprising an amphoteric pharmaceutical agent, an ion species selected from the group consisting of cationic hydroxide species and anionic hydrogen ion species, and a solvent system, the solvent system consisting essentially of a solvent selected from the group consisting of diethylene glycol monoethyl ether, polyglycerol oleate, alpha-hydro-w-hydroxypoly(oxyethylene)-poly(oxypropylene)-poly(oxyethylene) block co-polymers, and mixtures thereof, the ion species being capable of dissociating in the solution into pharmaceutically acceptable ions, the ion species being present in an amount such that between about 0.05 and less than about 1.5 moles of ions selected from the group consisting of hydrogen ions and hydroxide ions per mole of ionizable groups in the amphoteric pharmaceutical agent are present in the solution, the ion species partially ionizing the amphoteric pharmaceutical agent such that the amphoteric pharmaceutical agent is present in a dissolved state in the solution in both free form and as a salt in a solubility enhanced amount greater than the maximum solubility of the amphoteric pharmaceutical agent in the solution in the absence of the ion species.

* * * * *